(12) United States Patent
Danieli (10) Patent No.: US 10,293,017 B2
(45) Date of Patent: May 21, 2019

(54) METHODS AND COMPOSITIONS FOR TREATING AND PREVENTING LAMINITIS, FOUNDER AND OVEREATING IN AN UNGULATE

(71) Applicant: Ky Stockfeeds Pty Ltd., Kyabram, Victoria (AU)

(72) Inventor: Robert Danieli, Kyabram (AU)

(*) Notice: Subject to any disclaimer, the term of this patent is extended or adjusted under 35 U.S.C. 154(b) by 2 days.

(21) Appl. No.: 14/754,347

(22) Filed: Jun. 29, 2015

(65) Prior Publication Data
US 2015/0297665 A1 Oct. 22, 2015

Related U.S. Application Data

(62) Division of application No. 12/939,885, filed on Nov. 4, 2010, now abandoned.

(51) Int. Cl.
| | |
|---|---|
| *A61K 36/899* | (2006.01) |
| *A23K 10/18* | (2016.01) |
| *A23K 10/38* | (2016.01) |
| *A23K 10/30* | (2016.01) |
| *A23K 20/174* | (2016.01) |
| *A23K 20/158* | (2016.01) |
| *A23K 20/163* | (2016.01) |
| *A23K 20/22* | (2016.01) |
| *A23K 20/24* | (2016.01) |
| *A23K 20/26* | (2016.01) |
| *A23K 20/20* | (2016.01) |
| *A23K 50/20* | (2016.01) |
| *A23K 50/10* | (2016.01) |
| *A23K 50/30* | (2016.01) |

(52) U.S. Cl.
CPC ........... *A61K 36/899* (2013.01); *A23K 10/18* (2016.05); *A23K 10/30* (2016.05); *A23K 10/38* (2016.05); *A23K 20/158* (2016.05); *A23K 20/163* (2016.05); *A23K 20/174* (2016.05); *A23K 20/22* (2016.05); *A23K 20/24* (2016.05); *A23K 20/26* (2016.05); *A23K 20/30* (2016.05); *A23K 50/10* (2016.05); *A23K 50/20* (2016.05); *A23K 50/30* (2016.05); *Y02P 60/873* (2015.11)

(58) Field of Classification Search
None
See application file for complete search history.

(56) References Cited

PUBLICATIONS

Website Document entitled: "Equinews: Glycemic Index Among Horse Feeds". Dated Feb. 2, 2012. (available at http://www.equinews.com/article/glycemic-index-among-horse-feeds). Downloaded from website: Aug. 1, 2016.*
Website Document entitled: "Sugarcane Tops as Animal Feed by M.R. Naseeven". (available at http://www.fao.org/docrep/003/s8850e/S8850E10.htm). Downloaded from website: Aug. 1, 2016.*
Website Document entitled: "Feedipedia: Sugarcane tops". (available at http://www.feedipedia.org/node/558.*
Vervuert et al. (2006) Proceeding of 3rd European Equine Nutrition & Health Congress. pp. 1-9.*

* cited by examiner

*Primary Examiner* — Christopher R Tate
*Assistant Examiner* — Russell G Fiebig
(74) *Attorney, Agent, or Firm* — Gendloff IP; Elie Gendloff (57) ABSTRACT

The present invention relates to the production and use of feed compositions useful in the treatment and prevention of laminitis, founder and overeating, particularly in horses and ponies. The feed composition may reduce the effects of carbohydrate overload whilst providing a controlled release of metabolizable energy to avoid excessive fermentation and lactic acid production in the hind gut. At the same time the feed composition can provide nutrition to the animal whilst avoiding overeating. The combination of controlled bulk and energy provides for a feed composition that can control the symptoms of excess energy sources in the gut which may manifest as laminitis and founder.

11 Claims, 5 Drawing Sheets

METHODS AND COMPOSITIONS FOR TREATING AND PREVENTING LAMINITIS, FOUNDER AND OVEREATING IN AN UNGULATE

RELATED APPLICATIONS

The present application is a divisional of U.S. application Ser. No. 12/939,885, filed on Nov. 4, 2010, by Robert DANIELLI, and entitled "METHODS AND COMPOSITIONS FOR TREATING AND PREVENTING LAMINITIS, FOUNDER AND OVEREATING IN AN UNGULATE," the entire disclosure of which, including all the drawings, is incorporated by reference herein.

FIELD OF THE INVENTION

The present invention relates to the production and use of feed compositions useful in the treatment and prevention of laminitis, founder and overeating, particularly in horses.

BACKGROUND OF THE DISCLOSURE

Founder is one of the most crippling diseases of horses and ponies, which in severe and recurring cases, can reduce a horse's usefulness and lifespan. Laminitis, the initiating cause of founder, can affect any horse, of any age or sex, at any time of year. Although it is traditionally considered a disease of obese ponies, laminitis can be triggered by a variety of metabolic or physical causes in any horse.

Laminitis is typically caused by devitalization of the supporting laminae within the hoof of ungulates, leading to painful breakdown and tearing of the support tissues suspending the pedal bone within the hoof. If laminitis is not treated properly, the pedal bone drops or rotates downwards, resulting in founder, with total collapse causing severe lameness and risk of death.

Laminitis may be triggered by an upset in the fermentative processes in the gastrointestinal tract, whereby abnormally high amounts of lactic acid results in a condition known as hindgut acidosis. The excess acid destroys beneficial bacteria and leads to damage to the gut wall, thereby releasing endotoxins into the blood. It is these endotoxins that are thought to alter the blood circulation within the hooves, or cause the devitalization of the basement cells on the surface of the lamina.

Laminitis may be treated many ways and sometimes conservatively by confining the animal to a stable or small yard and often starving the animal. A sandy stall is preferred to allow the horse to stand as comfortably as possible. Furthermore, owners will often limit walking of a severely lame horse as further tearing and damage to the laminae will result.

Laminitis may also be treated using anti-inflammatory agents such as phenylbutazone ("bute") paste. Phenylbutazone is a prescription only medication, and cannot be used preventatively. Furthermore, this agent (like many anti-inflammatory drugs) can lead to side effects such as stomach perforation and allergic reactions. Other pharmaceutical agents that are often prescribed include sedatives, vasodilators and anti-clotting agents especially in the acute stages.

Physical therapy such as hoof support is often applied in an attempt to limit rotation of the pedal bone and other internal structural changes within the hoof. Support shoes which elevate the heels or 'heart bar' shoes which support the frog may be used. It is vital that these supportive shoes are correctly applied and regularly adjusted or they can cause excessive pressure and damage to the frog. In severe cases where shoes cannot be nailed on, support bandages or glue-on shoes may be used.

In some cases, calcium and biotin added to the feed for at least 6-12 months after an attack of laminitis helps to promote hoof growth, prevent broken away hoof edges and prevent separation at the white line during recovery. Horses with laminitis may also be commenced on Founderguard®, which is a granular feed additive with an antibiotic (virginiamycin) as the active component. The antibiotic may help to control overgrowth of the bacteria in the hindgut that produce lactic acid as they digest carbohydrate overload from grain or lush grass.

The use of Founderguard® is not without problems since some horses have, or develop allergies against the active component. Furthermore, the product poses exposure risks to humans with the material safety data sheet recommending the minimisation of dusts and the use of protective goggles, elbow-length gloves, facial protection and a mask or respirator.

A further problem of horses is that of overeating. While some animals will eat only what they need, the majority will overeat if given the opportunity. Ponies also easily become obese from overfeeding and therefore are at high risk for colic. Control of overeating is often more complex than simply providing less feed to the animal to consume. A number of horses, for example, may occupy a single paddock such that an overeating horse may consume a greater proportion of all feed on offer.

Hence it is a problem to provide a feed source that provides sufficient nutrition without the animal overeating or that will not lead to laminitis in highly susceptible ponies and horses. Furthermore, once the animal founders, there are no simple means to treat the animals and simultaneously provide sufficient nutrition without exacerbating the condition.

It is an aspect of the present invention to alleviate or overcome a problem of the prior art in providing compositions and methods useful in the treatment and/or prevention of laminitis, founder and overeating. The invention seeks to provide a simple feed composition that will prevent laminitis, founder and overeating and the feed composition may also be used to treat the conditions and eventually maintain the animal so as prevent further episodes of laminitis and founder or overeating.

A reference herein to any document or other matter which is given as prior art is not to be taken as an admission that that document or matter was known or that the information it contains was part of the common general knowledge as at the priority date of any of the claims.

SUMMARY OF THE INVENTION

In a first aspect the present invention provides an animal feed composition for the prevention or treatment of laminitis, founder or overeating in an ungulate animal, the composition comprising a graminaceous component, the graminaceous component having a slow release of energy and/or low energy density.

The feed composition reduces the effects of carbohydrate overload whilst providing a controlled release of metabolizable energy to avoid excessive fermentation and lactic acid production in the gut. At the same time the feed composition can provide nutrition and bulk to the animal whilst avoiding overeating.

In a second aspect the present invention also provides a method for producing an animal feed composition, the method comprising the step of adding a graminaceous component having a slow release of energy and/or low energy density to at least one other feed component.

In a third aspect the present invention provides a method of treating or preventing laminitis, founder or overeating in an ungulate animal, the method comprising administering to an ungulate animal in need thereof an effective amount of a feed composition as described herein.

In a preferred form of the method the feed composition is the major source of nutrition for the ungulate or is the only source of nutrition for the ungulate.

Throughout the description and claims of the specification, the word "comprise" and variations of the word, such as "comprising" and "comprises", is not intended to exclude other additives, components, integers or steps.

DETAILED DESCRIPTION OF THE EMBODIMENTS

Laminitis can be triggered by a variety of metabolic and physical causes. Most commonly, the disease is the end result of a digestive upset caused by over indulgent feeding practices, particularly heavy grain or lush pasture intake.

When horses and ponies eat low grain hard feeds and graze pasture with a low content of carbohydrates (starches and sugars) these energy sources are digested in the small bowel. However, if horses gorge on grains, or consume a high grain meal or hungrily graze a large bulk of lush pasture the excess carbohydrates that are not digested pass on into the large bowel. Fermentative bacteria in the large bowel rapidly increase in numbers to attack the carbohydrate mass to break it down.

This fermentation produces abnormally high amounts of lactic acid (hindgut acidosis) which in turn kills off other bacteria and damages the gut wall, releasing endotoxins that are absorbed into the blood. It is these endotoxins that are thought to alter the blood circulation within the hooves, or cause the devitalization of the basement cells on the surface of the lamina.

Accordingly, in a first aspect the present invention provides an animal feed composition for the prevention or treatment of laminitis, founder or overeating in an ungulate animal, the composition comprising a graminaceous component, the graminaceous component having a slow release of energy and/or low energy density.

The present invention provides a feed composition which reduces the effects of carbohydrate overload whilst providing a controlled release of metabolizable energy to avoid excessive fermentation and lactic acid production in the gut. At the same time the feed composition can provide nutrition and bulk to the animal whilst avoiding overeating. The combination of controlled bulk and energy provides for a feed composition that can control the symptoms of excess soluble carbohydrate in the gut which may manifest as laminitis and founder and protect the animal against further episodes of laminitis.

It has not been appreciated by prior artisans specifically that graminaceous components can contribute as an energy source, and moreover an energy source with a slow release of energy and/or low energy density such that a feed produced using such components would be useful in the treatment or prevention of laminitis, founder or overeating. Other classical feed sources such as grains and wheat have been preferred.

An energy source having a slow release of energy are sources that will be digested slowly and thereby release the energy slowly. Foods having the slow release may be those high in fiber and minerals which slow down the "quick release" of energy in the form of carbohydrates, proteins and fats. The high fiber component can also inherently contribute to the bulk providing a sensation of fullness. Graminaceous components that are low in soluble carbohydrates such as fructose are typically used in this invention. They can generally be high in complex carbohydrates that release their carbohydrates slowly.

In one embodiment, the feed composition comprises a graminaceous component that has a slow release of energy and a low energy density.

A feed composition having both of these features will satisfy the requirement to release the energy slowly thereby providing a controlled release of metabolizable energy to avoid excessive fermentation and lactic acid production in the gut and the low energy density nutrition and bulk to the animal whilst avoiding overeating. The combination of these features may break the cycle of recurring episodes of overeating, laminitis and founder.

An energy source having a low energy density is a source that has a large volume and fewer calories associated with it. The advantage is that the low energy density foods give a sensation of bulk whilst providing lower calories and the feeling of fullness. This may contribute to preventing overeating.

As used herein, the term "graminaceous" includes any species of grass within the Poaceae family. They may be described as herbaceous or woody plants with hollow or jointed stems and long narrow leaves such as, but not limited to, bamboo, reeds and sugar cane.

The feed compositions of the present invention may be a complete feed in that substantially all nutritional requirements of the subject animal are provided by the feed composition. However, it is to be understood that the term "feed composition" extends to feeds and feed supplements that provide less than the complete repertoire of nutrients.

The present compositions are suitable for the feeding of ungulates. The term "ungulate" is intended to mean any hoofed mammal, the hoof being characterized by the presence of two structures: the unguis (a scale-like plate; our finger- and toe-nails) and the subunguis (a softer layer, found as a very fine layer on the underside of our fingernails) which connect the unguis to the pad of the digit. Unlike claws and nails, hooves are the principal point of contact between the legs and the ground. In ungulates, the tough unguis encircles the tip of the digit as a cylinder, enclosing the subunguis within in. Since the unguis is harder than the subunguis, it does not wear down as quickly, resulting in a firm (sometimes sharp) leading edge to the hoof. The pads of the digits lie behind the hooves—these pads touch the ground in perissodactyls and some cetartiodactyls, while only the hooves bear weight in other ungulate cetartiodactyls (notably the Suiformes and Ruminantia). In many cetartiodactyls, only the central two digits touch the ground. Representative (but non-limiting) ungulates include the horse, zebra, donkey, cattle/bison, rhinoceros, camel, hippopotamus, goat, pig, sheep, giraffe, okapi, moose, elk, deer, tapir, antelope, and gazelle. The feed composition is particularly useful for treating horses and ponies.

As used herein, the term "laminitis" is intended to mean any acute or chronic inflammation of any or all of the digital laminae of the hoof of the ungulate animal. In the context of the present invention, the term is directed to any form of laminitis that may be treated or prevented using manipulation of the animal's diet. This includes laminitis caused by bacterial endotoxins (that may be released as a consequence of energy overload in the form of carbohydrates, proteins and/or fats) or insulin resistance. The laminitis in this situation will be a feed-induced laminitis.

In the context of the present invention the term "founder" is intended to mean a complication of laminitis, including the rotation or sinking of the PIII (coffin) bone in horses, or equivalent bone in other ungulates. Rotation occurs when the damage to the laminae is less severe and it will show up mainly in the toe area of the foot. One possible reason for this is the pull of the tendon attached to the coffin bone, the deep digital flexor tendon, literally pulling the dorsal face of the coffin bone away from the inside of the hoofwall. There are also ligaments attaching the collateral cartilages to the digit, primarily in the palmar portion of the foot, possibly contributing to a difference in support from front to back. Rotation results in an obvious misalignment between PII (the short pastern bone) and PIII (the coffin bone). In some cases, the rotation may also result in the tip of PIII penetrating the sole and becoming exposed externally. In some forms of founder the coffin bone pierces the bottom of the hoof (near the frog).

As used herein, the term "overeating" is intended to mean the overconsumption of feed by an animal, such that an aspect of the animal's health, well being or appearance is compromised. For example, overeating may lead to obesity, deposition of fat, insulin resistance, colic, equine metabolic syndrome and the like. In the case of feed induced laminitis, overeating may cause excessive overload of carbohydrates leading to the fermentation by the bacteria in the hind gut producing the endotoxins to trigger an onset of laminitis.

It is to be understood that the terms "treating" and "preventing" are not used in an absolute sense, and include circumstances where the animal is not completely cured or when the condition is not completely prevented.

The present invention provides that the graminaceous component of the feed has a slow release of energy and/or low energy density. The slow release of energy will be beneficial on its own by slowing the energy load such as in the form of carbohydrates so that in one theory, the lactic acid build-up is off set thereby limiting bacteria being killed off and the flow on effects of laminitis and founder. Additionally, the extended release of the energy provides for a prolonged nutritional effect. Components that are high in readily available energy sources such as glucose and fructose should be avoided.

The slow release of the carbohydrates, particularly in the form of glucose can be determined by the gylcaemic index (GI) of the food. For a slow release of energy, the GI must be low (low GI index).

Some feeds may also have high levels of highly soluble fructose. It is desirable to reduce the release of fructose from the feed. Ideally, if the fructose levels are reduced and a balance of the glucose/fructose is achieved possibly in the form of sucrose (less soluble), then this may assist in reducing the release of energy in the form of the more soluble fructose and glucose. Essentially, a slowdown of the release of easily digestible sugars and energy sources is desired.

Slow release of other energy sources such as proteins and fats can be determined by methods available to skilled addressee such as by measuring the release of calories from the breakdown of proteins and fats to amino acid and triglycerides. The skilled person is familiar with methods for measuring the glycemic index of a food. Such measurements are relative in nature, with a control food forming the basis of the assay. Representative methods are described in Ludwig, D. S. "The glycemic index" physiological mechanisms relating to obesity, diabetes, and cardiovascular disease. JAMA 2002, 287(18):2414-2423. Typically, blood samples for the determination of glucose are taken prior to eating and at regular intervals after eating over the next several hours. The changes in blood glucose over time are plotted as a curve. The glycemic index is calculated as the area under the glucose curve after the test food is eaten, divided by the corresponding area after the control food is eaten. The value is multiplied by 100 to represent a percentage of the control food. For example, a food may have a glycemic index of 76 relative to glucose, and 108 relative to white bread. This means that the blood glucose response to the carbohydrate in a baked potato is 76% of the blood glucose response to the same amount of carbohydrate in pure glucose and 108% of the blood glucose response to the same amount of carbohydrate in white bread. For horse feed, a control food may be any carbohydrate-rich food component such as oats or wheat grain.

In the context of the present invention, the term "low glycemic index" or "low GI" means that the index of the graminaceous component is low enough to treat or prevent laminitis, founder or overeating in the subject animal. The skilled artisan is able to identify the presence, absence and extent of laminitis and founder simply by looking at the hoof, and also watching the animal walking. Similarly, it is a simple matter to identify an animal that is overeating based on observations such as body weight and the deposition of fat. In one embodiment of the composition the glycemic index of the graminaceous component (based on a scale where oats=100) is less than a number selected from the group consisting of about 70, 65, 60, 55, 50, 45, 40, 35, 30, 25, 20, 15, 10, 9, 8, 7, 6, 5, 4, 3, 2, and 1. A GI of 55 or less is considered low. A range of 56 to 69 is considered to be medium and 70 is considered to be high. Hence, for the feed composition of the present invention it is ideal to use a graminaceous component having a GI in the range of 69 or less, preferably, 55 or less.

The present invention further provides in another embodiment that the graminaceous component has a low energy density. The low energy density of the graminaceous component provides fewer calories but greater bulk. This is beneficial in providing a feeling of satiety assisting the animal from overeating.

The measurement of energy density is well understood by the skilled person, involving assaying of the digestible energy content of a food and expressing that value per unit weight. Digestible energy can be measured by finding the gross energy of a food (using bomb calorimetry for example) and subtracting the gross energy of the feces of the subject animal fed for that food. Alternatively, digestible energy may be estimated by measuring the total digestible nutrient (TDN) content of the feed. TDN may be calculated as:

digestible crude protein (CP)+(digestible crude fat (EE)×2.25)+digestible cell wall (NDF)+digestible non-structural carbohydrate (NSC). NSC=100−CP−EE−NDF−ash.

The energy density of animal feeds is typically expressed as MJ/kg, and in one embodiment of the present feed compositions, the energy density is less than an amount selected from the group consisting of 10, 9, 8, 7, 6, 5, 4, 3, 2, and 1 MJ/kg. Ideally the energy density is less than 9 MJ/kg.

The combination of the slow release of energy and the low energy density of the graminaceous component provides an improved treatment for animals that have lost condition as a result of laminitis. It also provides for a gradual reduction of the body condition whilst managing hunger.

In one form of the invention, the graminaceous component is pre-treated to be devoid of seed, thus assisting to slow the energy release and/or lower the energy density of the feed composition as a whole. Graminaceous components such as but not limited to young hay (pre-seed formation), old hay (seeds removed), tropical grasses (seeds removed) and old sugar cane (seeds removed) may also be effective. The seeds can contain high levels of fructose and soluble carbohydrates. Reducing this component will enhance the prevention and treatment of laminitis.

The feed compositions of the present invention may in some instances further compromise graminaceous components that are not of a low glycaemic index or may contain high levels of soluble carbohydrates or are not of low energy density, and may further comprise non-graminaceous components such as oats, grains, fillers, meals, minerals, trace elements, oils, and the like. The skilled person is completely familiar with other feed components required to provide a complete feed, if that is desired, and is capable of formulating these additives accordingly so as to achieve the proper balance of a slow release of energy and/or low energy density, or a combination of high roughage and/or low soluble carbohydrate in the final feed composition.

Typically, the graminaceous component having a slow energy release and/or low energy density is present in a proportion 20-100% greater than that of any other single type of non-graminaceous component. Furthermore, the graminaceous component may be present in proportion of 20-100% greater than that of the sum of all other types of non-graminaceous components. In one form of the composition the graminaceous component provides the largest source of digestible energy in the feed composition. A person skilled in the art would be capable of determining an appropriate proportion of the graminacaous component so that the feed composition maintains an overall slow energy release and/or low energy density.

For instance, 100% graminaceous component such as sugar cane stalks could work as a feed composition, but it would not be ideal. Hence, adding non-graminaceous components can improve the feed composition.

In one embodiment of the composition, the graminaceous component is present in an amount of between about 20-100% of the feed composition. In another embodiment of the composition, the graminaceous component is present in an amount of about 20-70% of the feed composition.

The graminaceous component may be any member of the grasses that is capable of providing energy in accordance with the requirements for a slow release of energy and/or low energy density. In one embodiment the requirements are for a low level of soluble carbohydrates and/or low energy density. A reduction of the high soluble carbohydrates such as fructose is desired. This may be achieved by soaking in water, prior to adding to the feed composition to remove the soluble carbohydrates.

In another embodiment, the requirements for the feed composition are for low glycaemic index and/or low energy density. Hence this feed focuses on the glucose component of the feed. However, the general load of all available carbohydrates and generally soluble carbohydrates is important.

In one other form of the composition the graminaceous component is a perennial grass. In another embodiment of the invention the perennial grass is a member of the Tribe Andropogoneae, and in one form is a member of the Family Poaceae. In yet another embodiment of the composition the perennial grass is a member of the Genus *Saccharum*, and may be one or more of the following species: *Saccharum spontaneum, Saccharum robustum, Saccharum officinarum, Saccharum barbefi, Saccharum sinense*, and *Saccharum edule*.

In an alternative from of the invention the perennial grass is a member of the Genus *Sorghum*, and may any one or more of the following species: *Sorghum almum, Sorghum amplum, Sorghum angustum, Sorghum arundinaceum, Sorghum bicolour, Sorghum bicolor* subsp. *drummondii, Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum timorense, Sorghum trichocladum, Sorghum versicolor, Sorghum virgatum*, and *Sorghum vulgare*.

In some embodiments of the composition the perennial grass is a hybrid or cultivar of any of the perennial grass species of the genera *Saccharum* and *Sorghum* listed supra.

The graminaceous component may be treated or processed in any way to achieve a component having a slow energy release and/or a low energy density. In another embodiment, the component may have a low glycemic index and/or a low energy density. Ideally, the graminaceous component will have a low level of soluble carbohydrate such as fructose or glucose in combination with a low energy density.

For example, where the graminaceous component is sugar cane, the treatment or processing method typically includes harvesting the top of the sugar cane plant of approximately up to 1 meter or the first 2 to 3 feet and discharging the sap. The product being the whole plant or the stems may be mulched and desiccated, dried down and used directly or as part of the feed provided to the animal for the treatment of laminitis. The methods for treating preferably avoid separation of the sugar components of the cane from the non-sugar components, such as those implemented in the production of bagasse.

Characteristically, the feed composition of the present invention provides for a slow release of energy to the animal so as to avoid fermentation in the gut and build up of lactic acid. This can be achieved by removing the soluble carbohydrates such as fructose from the feed. Hence, it is possible to use graminaceous components that have been pre-treated such as by soaking in water, to remove most of the soluble carbohydrates.

The structure of the components or chaff may also provide the necessary hindrance to the release of the energy whilst providing bulk to induce a feeling of fullness. The roughage will achieve suitable gut fill. Hence, graminaceous components with complex carbohydrates are useful in the feed composition.

The length of the graminaceous component may also assist in the feed composition achieving the slow release of energy and to treat overeating. The length, if sufficiently long, can induce a chewing reflex which not only slowly releases the energy from the graminaceous component, but the chewing reflex can send messages back to the brain to indicate fullness. Ideally the length of the graminaceous component is long enough to induce a chewing action or reflex in the animal and may also provide sufficient roughage. The length of the graminaceous component may be 2-8 cm, or it may be about 6 cms.

In keeping with the aim of the invention to provide a feed useful in the treatment or prevention of laminitis, founder or overeating, the feed composition may be substantially devoid of soluble carbohydrates or a moderate or high glycaemic index/energy density carbohydrate source such as but not limited to oats, lucerne, molasses, young hay (with seeds) or wheat grains.

Further, optional, components of the feed composition include coloring agents such as carotenoids, astaxanthin, and lutein; aroma compounds; stabilisers; antimicrobial peptides; polyunsaturated fatty acids; reactive oxygen generating species; and/or at least one enzyme selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4.), phospholipase A1 (EC 3.1.1.32); phospholipase A2 (EC 3.1.1.4); lysophospholipase (EC 3.1.1.5); phospholipase C (EC 3.1.4.3); phospholipase D (EC 3.1.4.4); amylase such as, for example, alpha-amylase (EC 3.2.1.1); and/or beta-glucanase (EC 3.2.1.4 or EC 3.2.1.6).

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Usually fat- and water-soluble vitamins, as well as trace minerals form part of a so-called premix intended for addition to the feed, whereas macro minerals are usually separately added to the feed. The following are non-exclusive lists of examples of these components. Examples of fat-soluble vitamins are vitamin A, vitamin D3, vitamin E, and vitamin K, e.g. vitamin K3. Examples of water-soluble vitamins are vitamin B 12, biotin and choline, vitamin B1, vitamin B2, vitamin B6, niacin, folic acid and panthothenate, e.g. Ca-D-panthothenate. Examples of trace minerals are manganese, zinc, iron, copper, iodine, selenium, and cobalt. Examples of macro minerals are calcium, phosphorus.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In some embodiments, the animal feed composition of the invention contains at least one vegetable protein or animal protein source. Animal proteins may be derived from blood or offal, while vegetable proteins may be derived from legumes and cereals, for example materials from plants of the families Fabaceae (Leguminosae), Cruciferaceae, Chenopodiaceae, and Poaceae, such as soy bean meal, lupin meal and rapeseed meal. In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa. Other examples of vegetable protein sources are rapeseed, sunflower seed, cotton seed, and cabbage. Other examples of vegetable protein sources are cereals such as barley, wheat, rye, oat, maize (corn), rice, triticale, and sorghum.

The feed composition may take on any form such as but not limited to pellets or compound feed, or loose feed supplied as fodder. When the feed is provided in the form of pellets, the pellet may typically be a feed component without pre-treatment, or it may be soaked to create mulch. Nevertheless, the resulting feed will have the necessary slow release of energy and the low energy density necessary for the treatment and prevention of laminitis and founder. The pellet may furthermore have reduced soluble carbohydrates and increased roughage.

In a second aspect, the present invention provides a method for producing an animal feed composition, the method comprising the step of adding a graminaceous component having a slow release of energy and/or low energy density to at least one other feed component.

The slow release of energy may arise from substantial removal of the soluble carbohydrates such as but not limited to fructose and glucose or physically by the use of graminacoeus components that are not substantially processed and remain in a fibrous form. Graminaceous components of the form described herein may be used.

In another form of the method, the graminaceous component has a low glycemic index (GI) of less than about 70, 65, 60, 55, 50, 45, 40, 35, 30, 25, 20, 15, 10, 9, 8, 7, 6, 5, 4, 3, 2, or 1. A GI of 55 or less is considered low. A range of 56 to 69 is considered to be medium and 70 is considered to be high. Hence, it is ideal to use a graminaceous component having a GI in the range of 69 or less, preferably, 55 or less.

The method may further comprise the step of adding a non-graminaceous component, and preferably the graminaceous component is added to a final proportion of 20-100% greater than that of any other single type of non-graminaceous component. The graminaceous component may also be added to a final proportion 20-80% greater than that of the sum of all other types of non-graminaceous components.

In one embodiment of the method the graminaceous component is added to a final proportion of between 20 and 80% such that the graminaceous component provides the largest source of digestible energy in the feed composition. The graminaceous component may be added in an amount of between about 20 to 80% of the feed composition.

Before combining the feed components for the purposes of the present method, the graminaceous component may be pre-treated. Where the graminaceous component is sugar cane, only the top of approximately 1 meter or 2-3 feet of the stalk may be used. The stalk may be cut into shorter sections of approximately 8 to 10 cms or they may be about 6 cms to make eating easier for the animal. However, the graminaceous component should not be so small so as the cause a fast release of energy and no longer be able to provide the necessary bulk to induce a feeling of fullness. Similarly, the size of the graminaceous component may be large enough to induce a chewing reflex in the animal.

In a third aspect the present invention provides a method of treating or preventing laminitis, founder or overeating in an ungulate animal, the method comprising administering to an ungulate animal in need thereof an effective amount of a feed composition as described herein.

In a preferred form of the method the feed composition is the major source of nutrition for the ungulate or is the only source of nutrition for the ungulate.

In one embodiment of the method, the ungulate is a member of the Genus *Equus*, and in some forms is of the species *Equus ferus caballus*, or *Equus africanus asinus*, or a hybrid offspring of these species (such as a mule).

The present compositions and methods are particularly applicable to animals that are not working animals, such as pleasure horses and ponies. These animals do not have high energy requirements and benefit most from the slow release of energy and the low energy density or the low glycemic index/energy density feeds described herein.

The feed is typically administered to the animal once per day, but may be divided into smaller portions for feeding throughout the day. The animal should be commenced on the animal feed composition and monitored for improvement in laminitis, founder or overeating. Once a sufficient improvement or cure is noted, the animal may subsequently be fed on a maintenance feed (as described in the Examples herein) to prevent recurrence of the condition.

The present invention will now be more fully described by reference to the following non-limiting Examples.

EXAMPLES

Example 1: Complete Forage Feed Composition for the Prevention or Treatment of Laminitis, Founder or Overeating

| Feed Component | Amt (Kg/Metric Ton(MT) |
| --- | --- |
| Sugar cane | 410 |
| Lucerne chaff | 346 |
| Dehydrated distillers grains | 100 |
| Canola meal | 100 |
| Canola oil | 20 |
| Dolomitic limestone | 3 |
| Dicalcium phosphate | 4.5 |
| Magnesium sulphate | 4 |
| Sodium chloride | 12 |
| Additive mix* | 1 |
| Total | 1000.5 |

*includes Cu, Zn, Se, Mn, I, Co, Vitamins A, D, K, E, B6, B12, riboflavin, niacin, panthothenic acid, folic acid, and biotin.

This feed composition was found to have an energy density of 8.2 MJ/kg. This formulation meets or exceeds the nutritional requirements of mature horses and ponies as determined by the National Research Council (1989) in Nutrient Requirements of Horses. It is a very low energy density feed that provides bulk and slow release energy through natural healthy fermentation in the hindgut. It contains proteins and oils and ingredients high in mineral components of Glucose Tolerance factor. The chaff is cut long and in varying lengths to promote chewing and slow the rate of feed intake when compared with other chaffed or high grain feeds. The combination of very low energy density and slow release energy promotes gradual reduction in body condition while managing hunger.

This feed is complete feed for mature ponies and horses.

The feeding rate may depend on the body weight and may be feed in the following suggested rates:

| Bodyweight | Kg/day |
| --- | --- |
| 100 | 2.2 |
| 200 | 3.8 |
| 300 | 5.3 |
| 400 | 6.8 |
| 500 | 8.4 |
| 600 | 9.9 |

Example 2: Forage Feed Composition for the Prevention of Laminitis, Founder or Overeating, or for the Prevention of Relapse

| Feed Component | Amt (Kg/Metric Ton(MT) |
| --- | --- |
| Mixture of graminaceous chaff | 605 |
| Lucerne chaff | 200 |
| Dehydrated distillers grains | 100 |
| Canola meal | 50 |
| Canola oil | 20 |
| Dolomitic limestone | 3 |
| Dicalcium phosphate | 5 |
| Magnesium sulphate | 4 |
| Sodium chloride | 12 |
| Additive mix* | 1 |
| Total | 1000 |

*includes Cu, Zn, Se, Mn, I, Co, Vitamins A, D, K, E, B6, B12, riboflavin, niacin, panthothenic acid, folic acid, and biotin.

This feed composition was found to have an energy density of 9.1 MJ/kg. This formulation meets or exceeds the nutritional requirements of mature horses and ponies as determined by the National Research Council (1989) in Nutrient Requirements of Horses. It is a very low energy density feed that provides bulk and slow release energy through natural healthy fermentation in the hindgut. It contains proteins and oils and ingredients high in mineral components of Glucose Tolerance factor. The chaff is cut long and in varying lengths to promote chewing and slow the rate of feed intake when compared with other chaffed or high grain feeds. The combination of very low energy density and slow release energy promotes gradual stable body condition while managing hunger.

This feed is complete feed for mature ponies and horses. It may be fed as a complete feed to breeding mares or growing horses or used to complement a feeding program.

The feeding rate may depend on the body weight and may be feed in the following suggested rates:

| Bodyweight | Kg/day |
| --- | --- |
| 100 | 2.0 |
| 200 | 3.4 |
| 300 | 4.7 |
| 400 | 6.1 |
| 500 | 7.5 |
| 600 | 8.9 |

Example 3: Preparation of Feed Composition (a) Graminaceous component from Sugar Cane (the graminaceous component) may derive from sugar cane. Approximately up to 1 meter or the first 2 to 3 feet of the sugar cane plant is harvested and the sap is discharged. However, the whole plant may also be used.

The whole plant or the stems are then mulched and desiccated. The stems are mulched to varying lengths in the range of approximately 2 to 8 cm, averaging 6 cm. This is a length that when eaten by the animal should induce a chewing reflex to slowly release the food and hence energy from the graminaceous component.

The stems and the stalks will provide for the low energy density and hence bulk to the feed composition to assist in preventing overeating.

The mulch can then be used directly or made into pellets directly. The size of the pellets may be as small as 2 mm or optionally 4-5 mm in diameter. They can be pelletized to any size or even made into cubes of 1 inch in size. Importantly, they are made to a size that can be eaten by the animal and effect a chewing motion. Further additives such as coloring agents, fatty acids, reactive oxygen generating species, fat- and water-soluble vitamins, trace minerals, and vegetable protein or animal protein sources may be included at this point prior to making pellets.

Example 4: Treatment of Overeating in a Horse

Figure 1:
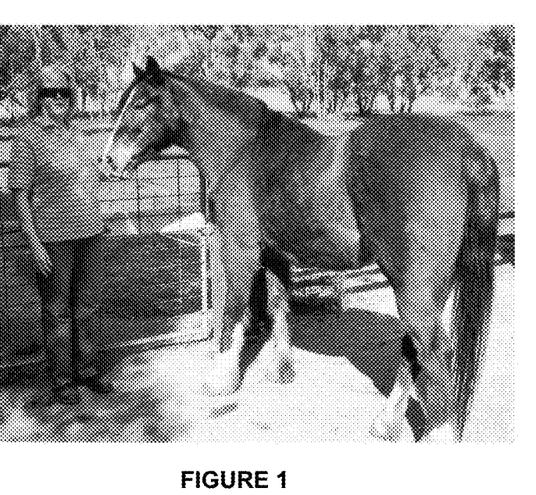
FIGS. 1 and 2 are photographs showing "Indi" weighing approximately 365 kg after treatment with the food composition.
Figure 2:
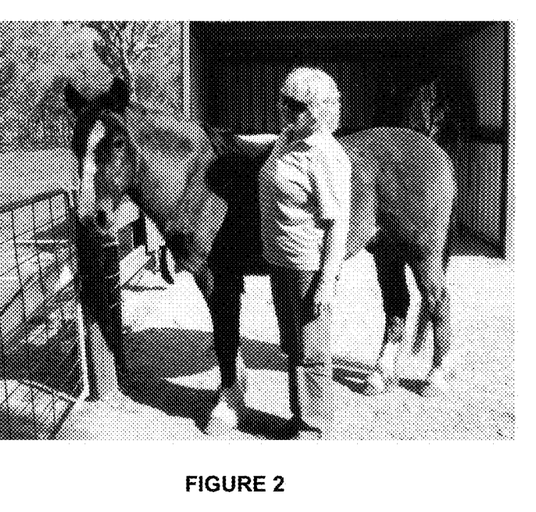

"Indi" is a 13 year old male Welsh cob-type pony.
Condition
"Indi" presented as overweight and weighing approximately 445 kg. Indi had two bouts of laminitis and was on phenylbutazone (Bute). The aim was to drop his weight without starving him.
Method
Indi was started on a forage feed composition as in Example 1 supplemented with oaten hay and kept off green grass. At this stage, he was not suffering from laminitis. The forage feed composition of Example 1 was to help him lose weight. The feed was provided to him on at least twice a day. However, he could be fed more but he would not be hungry due to the feed composition.
Result
After six months of feeding Indi a mix of the forage feed composition as in Example 1, and forage feed composition as in Example 2 and oaten hay have managed to drop his weight to 365 kg (FIGS. 1 and 2). While on this feeding system, Indi remained laminitis free. Indi will continue to be fed the complete forage feed compositions of Example 1 and 2 to keep him in riding condition.

Example 5: Treatment of Overeating in a Pony

Figure 3:
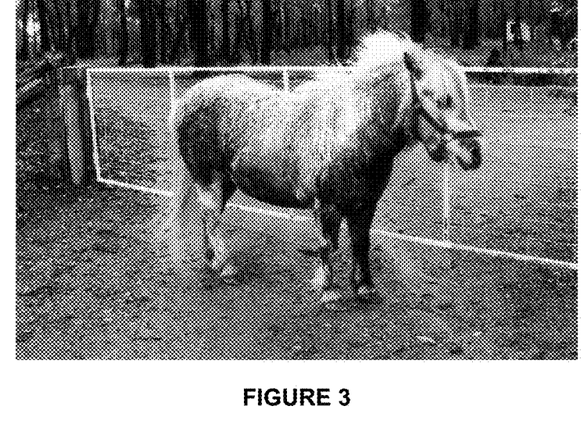
FIGS. 3 and 4 are photographs showing "Blue" after food composition treatment where he remains laminitis free and has lost weight and is in good condition.
Figure 4:
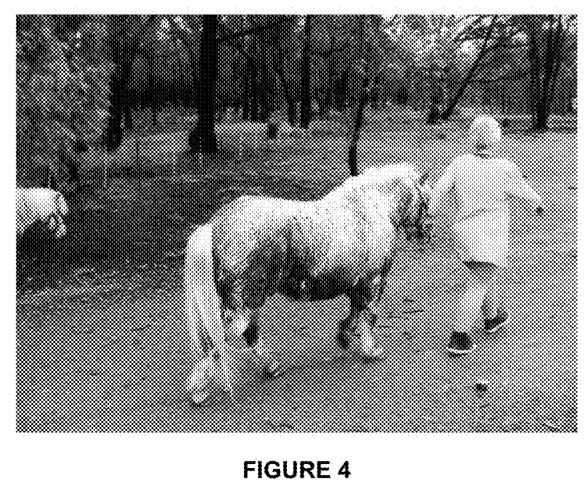

"Blue" is a six year old male Shetland cob-type pony.
Condition
Blue was overweight to the point of extreme obesity. He had already had two bouts of laminitis, was on phenylbutazone (Bute) intermittently and limped constantly. Due to being in constant pain he also had bad temper and was obviously unhappy.
Method
Blue was started on the forage feed composition of Example 1 in November 2009. He initially did not like the feed but after five days was eating well and commenced to consistently loose 1 cm a week from his girth. He was kept off green grass in a smallish yard. He was fed three times a day in sufficient quantity that he began to not eat all the feed provided. Feeding was then kept at this level. For the last four months he has been in a paddock which has very little feed and fed the forage feed composition of Example 1 twice daily with extra if it is cold or wet or if he looked hungry.
Result
After eleven months of feeding Blue on the forage feed composition of Example 1 he remains laminitis free (FIGS. 3 and 4). He is now a happy good natured pony who runs and trots freely. He does not limp and is fit and in a lovely condition. He is even able to have the occasional treat. Blue will continue to be fed the forage feed composition of Example 1 to keep him in good condition and not hungry.

Example 6: Treatment of Laminitis in a Horse

Figure 5:
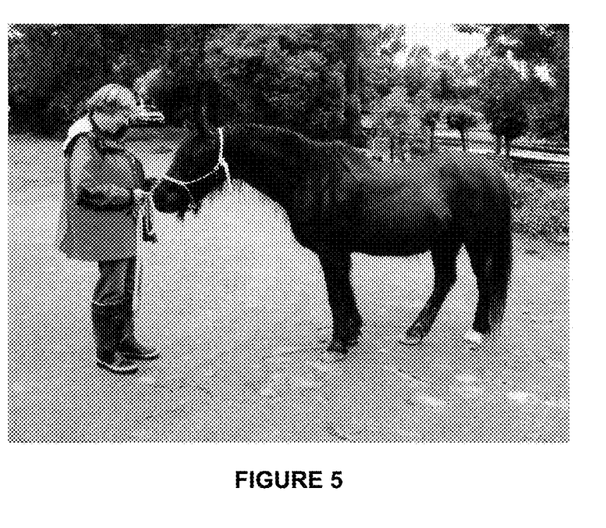
FIGS. 5 and 6 are photographs showing "Sammy" improved after food composition treatment.
Figure 6:
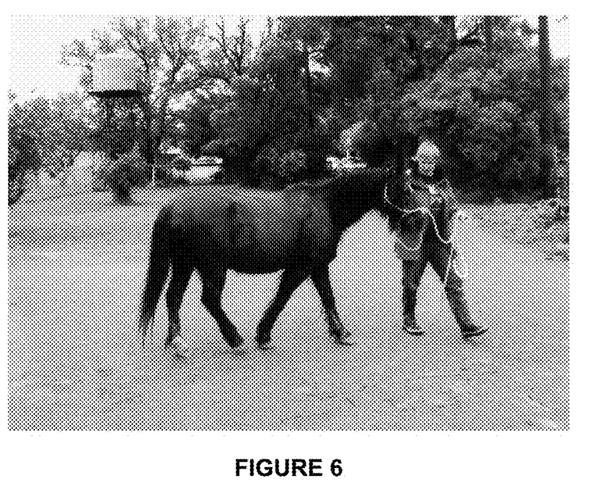

"Sammy" is a 25 year old Welsh B Gelding.
Condition
Prior to commencing feeding with the forage feed composition of Example 1, Sammy developed chronic laminitis. He was under continual Veterinary care and was on high doses of phenylbutazone (Bute) and various different feeds were tried unsuccessfully to treat laminitis. Permanent medication or euthanasia seemed to be the only options if the right feed was unable to be found.
Method
Sammy was put onto the forage feed composition of Example 1 in November 2009. His condition improved quickly and he has been laminitis and Bute free since (FIGS. 5 and 6). He now has the forage feed composition of Example 1 with a very small quantity of Speedi-beet fed twice daily.
Result
Sammy is no longer hungry and is in good condition.

Example 7: Treatment of Founder in a Pony

Figure 7:
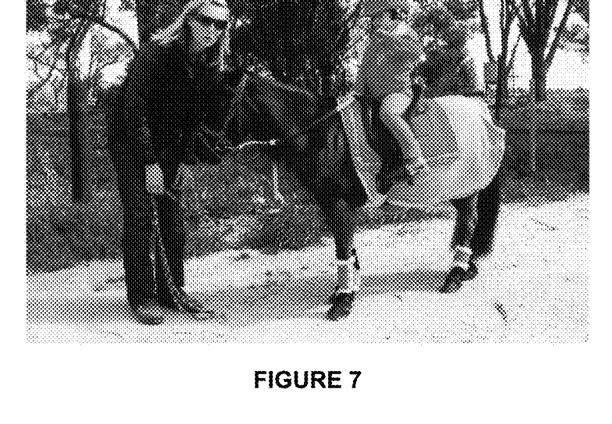
FIGS. 7 and 8 are photographs showing "Waspee" after six months on food composition treatment.
Figure 8:
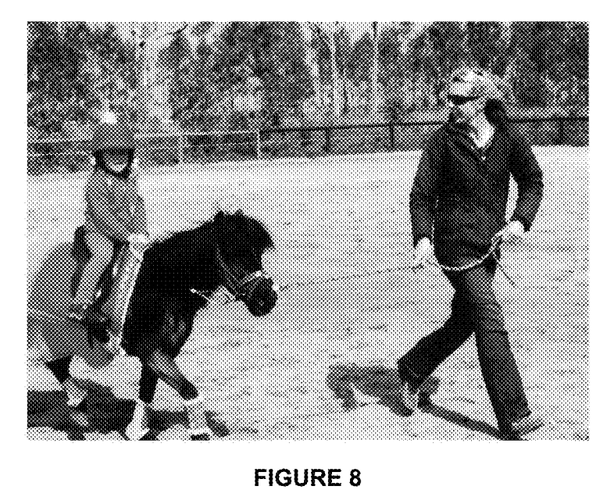

"Waspee" is a 20 year old male Shetland pony.
Condition
Waspee was very lean and unable to eat virtually anything without foundering. He would lie down all the time as he was in so much pain and was constantly on phenylbutazone (Bute). His condition score was rated as 2/5. He was under Veterinary supervision and they were unable to improve his quality of life. Euthanasia was an option.
Method
Waspee was put in a yard without any grass and fed only on the complete forage feed compositions of Example 1 and water. His improvement was immediate although he was still on phenylbutazone at this stage. Two weeks later he was taken off Bute and consumed a blend of the complete forage feed composition of Example 1 and Example 2 and started to gain weight. After this stage, some clover/rye hay was introduced into the diet.
Result
Six months on Waspee now has a condition score of 4/5 (FIGS. 7 and 8). He is on the complete forage feed of Example 2 and some pasture hay. Bute is now only required when the farrier does his hooves.

Example 8: Treatment of Overeating and Obesity in a Horse

"Phoebie" is a 10 year old female Cleveland Bay cross horse.
Condition
Phoebie was obese and prone to founder very easily. Having already survived a serious founder event five years ago where her pedal bone had rotated through the soles of her hooves, a means to feed her and prevent another founder event was sought.

Method

In October 2009, Phoebie was placed on the forage feed composition of Example 1 and some grass hay for weight loss and laminitis prevention.

Result

Figure 9:
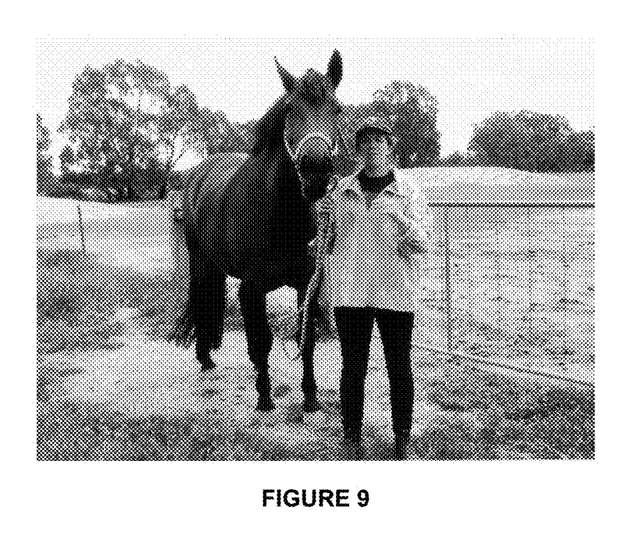
FIGS. 9 and 10 are photographs showing "Phoebie" following food composition treatment and having lost weight.
Figure 10:
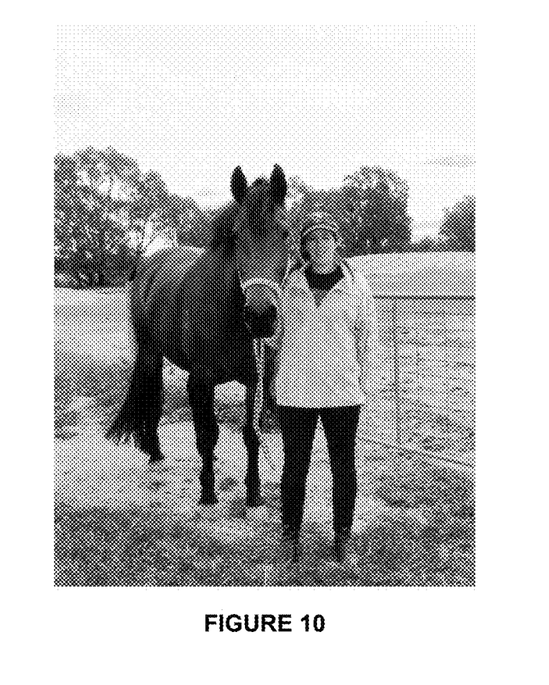

Over 12 months, Phoebie has remained laminitis free and has trimmed down to an ideal size (FIGS. 9 and 10).

Example 9: Treatment of Laminitis and Founder and Overeating in a Pony

"Cra-mer Park Brandysnap" is a 6 year old female 78 cm Miniature Pony.

Condition

In October 2009 Cra-mer Park Brandysnap was slightly overweight and had chronically foundered. She couldn't walk and was lying down. She had previously founded on meadow grass and there was no satisfactory means to treat her foundering.

Method

Cra-mer Park Brandysnap was fed on the complete forage feed composition of Example 1. After just three days on the forage feed composition she was up and walking well. The pony was then kept on the forage feed composition of Example 1 with some additional oaten chaff that was free of oat seeds.

Result

Cra-mer Park Brandysnap has been on this feed system for almost 12 months and has remained laminitis free and has dropped some weight as well. The feed has also prevented stomach ulcers and she is never starved of feed.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as broadly described herein.

What is claimed is:

1. A method of treating laminitis or founder in a horse or pony having laminitis or founder, the method comprising administering to the horse or pony a feed composition comprising effective amounts of:
   (a) a graminaceous component, in an amount of about 41 to 60.5% of the feed composition; and
   (b) one or more carbohydrate sources selected from the group consisting of oats, alfalfa, molasses, young hay (without seeds), wheat grains and wheat seeds,
   wherein the graminaceous component is a sugar cane plant selected from the group consisting of *Saccharum spontaneum, Saccharum robustum, Saccharum officinarum, Saccharum barberi, Saccharum sinense*, and *Saccharum edule*,
   wherein the graminaceous component has a glycemic index of less than about 69, and
   wherein the feed composition provides greater than 50% of the nutrition for the horse or pony.

2. The method according to claim 1 wherein the graminaceous component comprises the top of a sugar cane plant excluding the stalk.

3. The method according to claim 1 wherein the graminaceous component comprises sugar cane stalks.

4. The method according to claim 1, wherein the energy density of the feed composition is less than about 10 MJ/kg.

5. The method according to claim 1, wherein the feed composition is an only source of nutrition for the horse or pony.

6. The method according to claim 1, wherein the horse or pony is a member of the Genus *Equus*, or wherein the horse or pony is of the species *Equus ferus caballus*, or *Equus africanus asinus*, or a hybrid offspring of these species.

7. The method according to claim 1, wherein the graminaceous component provides the largest source of digestible energy in the feed composition.

8. The method according to claim 1, wherein the carbohydrate source is alfalfa.

9. The method according to claim 1, wherein the graminaceous component is sugar cane that is mulched and desiccated, in varying lengths in the range of approximately 2 to 8 cm.

10. The method according to claim 1, wherein the graminaceous component and/or the carbohydrate source is cut to varying lengths such that chewing is promoted.

11. The method according to claim 1, wherein soluble carbohydrates in the graminaceous component are removed before administering the feed.

* * * * *